United States Patent [19]

Takeuchi et al.

[11] Patent Number: 5,409,877
[45] Date of Patent: Apr. 25, 1995

[54] CATALYST FOR PRODUCING ALDEHYDE AND ALCOHOL FROM OLEFIN, CARBON MONOXIDE AND HYDROGEN

[75] Inventors: Kazuhiko Takeuchi; Takaaki Hanaoka; Takehiko Mastuzaki, all of Tsukuba; Yoshihiro Sugi, Matsudo; Hiroyuki Asaga, Ichihara; Yoshimoto Abe, Noda; Takahisa Misono, Kawaguchi, all of Japan

[73] Assignee: Director-General of Agency of Industrial Science and Technology, Japan

[21] Appl. No.: 931,965

[22] Filed: Aug. 19, 1992

[30] Foreign Application Priority Data

Aug. 22, 1991 [JP] Japan ................................. 3-235570
Oct. 11, 1991 [JP] Japan ................................. 3-335795

[51] Int. Cl.⁶ .......................... B01J 21/08; B01J 23/89
[52] U.S. Cl. .................................. 502/245; 502/243; 502/260; 502/237
[58] Field of Search ............... 502/326, 331, 330, 325, 502/241, 245, 243, 260, 327, 237, 170; 568/451

[56] References Cited

U.S. PATENT DOCUMENTS

| | | | |
|---|---|---|---|
| 2,500,210 | 3/1950 | Schexnailder | 502/237 |
| 3,759,823 | 9/1973 | Davies et al. | 502/327 X |
| 3,787,332 | 1/1974 | Sugier | 502/245 X |
| 4,122,110 | 10/1978 | Sugier et al. | 502/331 X |
| 4,396,539 | 8/1983 | Sapienza et al. | 502/326 |
| 4,654,321 | 3/1987 | Pesa et al. | 502/331 |
| 4,752,623 | 6/1988 | Stevens et al. | 502/241 |
| 5,086,030 | 2/1992 | Bjornson et al. | 502/241 |
| 5,102,851 | 4/1992 | Eri et al. | 502/327 X |

FOREIGN PATENT DOCUMENTS

| | | | |
|---|---|---|---|
| 0610558 | 6/1978 | U.S.S.R. | 502/327 |
| 0600765 | 1/1982 | U.S.S.R. | 502/327 |
| 90007377 | 7/1990 | WIPO | 502/327 |

OTHER PUBLICATIONS

*Catalog Handbook of Fine Chemicals*, Aldrich Chemical Company, Inc., 1990, Milwaukee, Wisc., pp. 1149–1151 Month of publication is unknown.
Kirk–Othmer, *Encyclopedia of Chemical Technology*, 3rd ed., John Wiley & Sons, 1982, vol. 20, pp. 766–781. Month of publication is unknown.
*Biochemicals and Organic Compounds for Research and Diagnostic Reagents*, Sigma Chemical Company, 1992, pp. 905–907. Month of publication is unknown.
*Alfa Catalog*, Morton Thiokol, Inc., 1986, pp. 510–512. Month of publication is unknown.

*Primary Examiner*—Paul Lieberman
*Assistant Examiner*—Douglas J. McGinty
*Attorney, Agent, or Firm*—Lorusso & Loud

[57] ABSTRACT

A catalyst for hydroformylation of an olefin with $H_2$ and CO is disclosed which includes an inorganic oxide carrier, and two or more catalytic metal components supported on the carrier, the metals of said catalytic metal components being cobalt and at least one auxiliary metal selected from rhodium, ruthenium, rhenium, iridium, platinum, palladium, copper, osmium and gold. By contacting a feed of an olefin, $H_2$ and CO with the catalyst, the olefin is converted into an aldehyde and an alcohol.

2 Claims, No Drawings

CATALYST FOR PRODUCING ALDEHYDE AND ALCOHOL FROM OLEFIN, CARBON MONOXIDE AND HYDROGEN

BACKGROUND OF THE INVENTION

1. Field of the Invention

This invention relates generally to a novel composite catalyst and, more specifically, a catalyst including an inorganic oxide carrier and catalytic metal components supported thereon and useful for the production of an alcohol and an aldehyde by hydroformylation of an olefin with CO and $H_2$. The present invention is also directed to a method of producing an alcohol and an aldehyde using the above catalyst.

2. Description of the Prior Art

As supported catalyst to be used for the hydroformylation of an olefin, there have thus far been proposed a catalyst containing rhodium supported on zeolite (J. Catal., 75, 188(1982)), a catalyst containing selenium-modified rhodium supported on zirconia (J. Chem.. Soc., Chem. Commun., 1327(1988)) and a catalyst containing rhodium supported on silica (Chem. Lett., 1917(1988)). These catalysts, which contain expensive rhodium as a major catalytic component, show a hydroformylation selectivity of as low as 40%.

As hydroformylation catalysts in which rhodium is not present or is a minor component, there have been proposed a catalyst containing nickel supported on an inorganic oxide (Proceedings of 9th International Congress on Catalysis, 513(1988)), a catalyst containing palladium, ruthenium, platinum, nickel or rhodium which is modified with sodium (Catalyst, 30, 488(1988) and J. Chem. Soc., Chem. Commun., 1403(1989)), a catalyst containing a ruthenium cluster or ruthenium-cobalt clusters, such as $[NEt_4][HRu_3(CO)_{11}]$, $[NEt_4][Ru_3(CO)_{13}]$, $H_3Ru_3Co(CO)_{13}$ or $HRuCo_3(CO)_{12}$, supported on activated carbon (Chem. Lett., 941(1987)) and a catalyst containing a triruthemiumketenylidene cluster of $[PPN]_2[Ru_3(CO)_9(CCO)]$ supported on magnesia, silica or silica-alumina (Catal. Lett., 6, 361(1990)). With these catalysts, however, hydrogenation of olefins proceeds more rapidly than hydroformylation so that saturated hydrocarbons are produced as a major product with a low yield of the desired aldehyde and alcohol.

SUMMARY OF THE INVENTION

It is, therefore, the prime object of the present invention to provide a novel catalyst which is relatively inexpensive but which can yield desired alcohol and aldehyde with a high yield and a high selectivity.

Another object of the present invention is to provide a process for the production of alcohol and aldehyde by hydroformylation of an olefin with carbon monoxide and hydrogen gas.

In accomplishing the foregoing objects, the present invention provides a catalyst including an inorganic oxide carrier, and two or more catalytic metal components supported on the carrier, wherein the metals of the catalytic metal components are a combination of cobalt and at least one auxiliary metal selected from the group consisting of rhodium, ruthenium, rhenium, iridium, platinum, palladium, copper, osmium and gold.

In another aspect, the present invention provides a method of producing an aldehyde and an alcohol, which comprises contacting a raw material feed containing an olefin, carbon monoxide and hydrogen with the above catalyst at a temperature of 100–250° C.

Other objects, features and advantages of the present invention will become apparent from the detailed description of the preferred embodiments of the invention to follow.

DETAILED DESCRIPTION OF THE PREFERRED EMBODIMENT OF THE INVENTION

The catalyst of the present invention is composed of an inorganic oxide carrier, and two or more catalytic metal components supported on the carrier.

Any known inorganic oxide carrier may be used for the purpose of the present invention. Examples of suitable inorganic oxide carriers include silica, silica gel, alumina, amorphous silica-alumina, zeolite, silicalite, zirconia, titania, magnesia, calcia, strontium oxide, barium oxide, niobium oxide and neodymium oxide. The carrier is generally in the form of granule, pellet, powder or any other shaped body and preferably has a specific surface area of 0.1–1000 m$^2$/g and a total pore volume of 0.1–100 cc/g.

Supported on the above inorganic oxide carrier are catalytic metal components, the metals of which are cobalt and at least one auxiliary metal selected from rhodium, ruthenium, rhenium, iridium, platinum, palladium, copper, osmium and gold.

The composite catalyst may be prepared by a method including the steps of impregnating the above inorganic oxide carrier with a solution containing a cobalt compound and a compound of the auxiliary metal, drying the metal compound-bearing carrier, and subjecting the dried carrier to a reducing condition at an elevated temperature.

The cobalt compound and auxiliary metal compound may be each in the form of, for example, an acetate, a nitrate, a halide, a carbonyl, an oxide or a diammine complex. The cobalt compound and the auxiliary metal compound are each dissolved in an aqueous or an organic liquid. The inorganic carrier is then immersed in each of the resulting solutions to impregnate the carrier therewith. If desired, the cobalt and auxiliary compounds may be dissolved altogether in a suitable solvent and the carrier may be impregnated with the solution containing both compounds.

In the case of a volatile compound of cobalt or the auxiliary metal, such as triruthenium dodecacarbonyl, it is possible to support the compound as such on the carrier without dissolving into a solvent. In such a case, a reduced pressure is suitably used to facilitate the deposition of the catalytic compound on the carrier.

The total amount of the catalytic metal compounds to be supported on the carrier is generally in the range of 0.1–30% % by weight, preferably 0.3–10% by weight, in terms of elemental metals, based on the weight of the carrier. The amount of the auxiliary metal relative to cobalt is preferably such as to provide an atomic ratio of auxiliary metal to cobalt of 0.001–10, more preferably 0.002–5.

In use, the catalyst having the catalytic metal compounds supported on the carrier is preferably contacted with a reducing gas such as $H_2$ or CO at an elevated temperature, generally at 100°–600° C., preferably 300°–500° C., so that at least part of the catalytic metal compounds is converted into elemental metals. In the catalyst according to the present invention, the catalytic components supported on the carrier are preferably in the form of elemental metals or in the state were the catalytic components are chemically bonded to oxygen atoms of the carrier.

Any olefin may be used as a raw material for the catalytic hydroformylation of the present invention. Generally, an olefin having 2-20 carbon atoms is used. Illustrative of suitable olefins are aliphatic olefins such as ethylene, propylene, butene, butadiene, pentene and hexene; alicyclic olefins such as cyclobutene, cyclopentene, cyclohexene, cyclopentadiene or cyclooctadiene; and aromatic olefins such as styrene, indene, stilbene and methylstyrene.

The catalytic hydroformylation according to the present invention proceeds as follows:

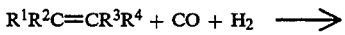

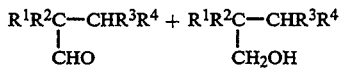

wherein $R^1$, $R^2$, $R^3$ and $R^4$ each represents an organic radical. When the raw material olefin is in the form of a gas, a gas mixture containing CO, $H_2$ and the olefin is preferably continuously contacted with the catalyst which is in the form of a packed bed or a fluidized bed. When the olefin is in the form of a liquid, the reaction may be carried out by contacting a liquid olefin, which may be diluted in a suitable inert solvent, with the packed catalyst together with CO and $H_2$. If desired, a batch system may be adopted.

The reaction is performed at a temperature of 100°-250° C., preferably 120°-210° C. The reaction pressure is preferably 5-100 kg/cm$^2$, more preferably 8-50 kg/cm$^2$. The reaction time is preferably 100-10000 leter/leter hour in terms of gas hourly space velocity.

The following examples will further illustrate the present invention.

EXAMPLE 1

Granular silica gel (100 g) was placed in a flask and heated at 200° C. for 2 hours under vacuum. An aqueous solution containing 84.8 mmol of cobalt acetate (Co(OCOCH$_3$)$_2$.4H$_2$O) was then fed to the above flask. The thus impregnated silica gel was then dried at 120° C. under vacuum for 2 hours and subsequently treated at 300° C. for 3 hours in the atmosphere of hydrogen to obtain a Co-carrying catalyst named Co(A)/SiO$_2$.

A quantity of the Co(A)/SiO$_2$ catalyst was mixed with 6.73 mmol of tetrairidium dodecacarbonyl (Ir$_4$(CO)$_{12}$) and the mixture was stirred at 150° C. under vacuum. The resulting mixture was then heated at 450° C. under an atmosphere of hydrogen for 3 hours to give a Co,Ir-containing catalyst (named Co(A)-Ir(CO)/SiO$_2$) having Co and Ir contents of 5 parts by weight and 5.16 parts by weight, respectively, per 100 parts by weight of the silica gel carrier.

The Co(A)-Ir(CO)/SiO$_2$ was packed in a stainless steel tubular reactor. After a further hydrogen treatment at 450° C. for 3 hours, a mixed gas (Feed Gas (A)) consisting of 10 parts by volume of Ar, 30 parts by volume of CO, 30 parts by volume of H$_2$ and 30 parts by volume of C$_2$H$_2$ was fed to the reactor to effect the hydroformylation of ethylene. The reaction conditions were as shown in Table 1. The product gas discharged from the reactor was introduced directly into gas chromatographs to measure the conversion of ethylene and the selectivities. The results are summarized in Table 2.

In Table 2, ethylene conversion and selectivity are defined as follows:

$$\text{Conversion}(\%) = (M - R)/M \times 100$$

wherein M represents the amount (mole) of ethylene fed to the reactor, R represents the amount (mole) of unreacted ethylene discharged from the reactor, $$\text{Selectivity}(\%) = P/(M - R) \times 100$$

wherein P represents the amount (mole) of the product concerned and M and R are as defined above.

In Table 1, 2-methyl-2-pentanal and 2-methylpentanal are condensation products of propionaldehyde and 2-methyl-1-pentanol is a hydrogenation product of the condensation product.

Similar tests were further performed using two different mixed gases (Feed Gas (B) consisting of 10 parts by volume of Ar, 50 parts by volume of CO, 10 parts by volume of H$_2$ and 30 parts by volume of C$_2$H$_2$; and Feed Gas (C) consisting of 10 parts by volume of Arc, 55 parts by volume of CO, 5 parts by volume of H$_2$ and 30 parts by volume of C$_2$H$_2$). The results are also shown in Table 2.

EXAMPLE 2

Example 1 was repeated in the same manner as described except that the amount of the iridium compound was changed to obtain a Co,Ir-containing catalyst (Co(A)-Ir(CO)/SiO$_2$) having Co and Ir contents of 5 parts by weight and 2.06 parts by weight, respectively, per 100 parts by weight of the silica gel carrier. Using this catalyst, Feed Gas (A) was reacted under the conditions summarized in Table 1 to give the results shown in Table 2.

EXAMPLES 3-5

A quantity of the Co(A)/SiO$_2$ catalyst was mixed with an aqueous solution containing a quantity of iridium chloride (IrCl$_3$.xH$_2$O) and the mixture was stirred under vacuum, dried and treated with hydrogen to give a Co,Ir-containing catalyst (named Co(A)-Ir(Cl)/SiO$_2$) having a Co content of 5 parts by weight and an Ir content of 5.16 (Example 3), 2.06 (Example 4) or 0.50 (Example 5) parts by weight per 100 parts by weight of the silica gel carrier. Using these catalysts, Feed Gas (A) was reacted under the conditions summarized in Table 1 to give the results shown in Table 2.

EXAMPLE 6

Granular silica, gel (100 g) was placed in a flask and heated at 200° C. for 2 hours under vacuum. An aqueous solution containing 84.8 mmol of cobalt nitrate (Co(NO$_3$)$_2$.6H$_2$O) was added to the above flask. The thus impregnated silica gel was then dried and treated with hydrogen in the same manner as that in Example 1 to obtain a Co-carrying catalyst named Co(N)/SiO$_2$. The Co(N)/SiO$_2$ catalyst was mixed with a quantity of tetrairidium dodecacarbonyl (Ir$_4$(CO)$_{12}$) and the mixture was treated with hydrogen in the same manner as that in Example 1 to give a Co,Ir-containing catalyst (named Co(N)-Ir(CO)/SiO$_2$) having Co and Ir contents of 5 parts by weight and 2.06 parts by weight, respectively, per 100 parts by weight of the silica gel carrier. Feed Gas (A) was reacted in the presence of this catalyst under the conditions summarized in Table 1 to give the results shown in Table 2.

EXAMPLE 7

Granular silica gel (100 g) was placed in a flask and heated at 200° C. for 2 hours under vacuum. An aqueous solution containing 84.8 mmol of cobalt chloride ($COCl_2.6H_2O$) was added to the above flask. The thus impregnated silica gel was then dried and treated with hydrogen in the same manner as that in Example 1 to obtain a Co-carrying catalyst named $Co(Cl)/SiO_2$. The $Co(Cl)/SiO_2$ catalyst was mixed with a quantity of tetrairidium dodecacarbonyl ($Ir_4(CO)_{12}$) and the mixture was treated with hydrogen in the same manner as that in Example 1 to give a Co,Ir-containing catalyst (named $Co(Cl)-Ir(CO)/SiO_2$) having Co and Ir contents of 5 parts by weight and 2.06 parts by weight, respectively, per 100 parts by weight of the silica gel carrier. Feed Gas (A) was reacted in the presence of this catalyst under the conditions summarized in Table 1 to give the results shown in Table 2.

Comparative Example 1

Using the $Co(A)/SiO_2$ catalyst obtained in Example 1, Feed Gas (A) was reacted under the conditions summarized in Table 1 to give the results shown in Table 2.

Comparative Example 2

Using the $Co(N)/SiO_2$ catalyst obtained in Example 6, Feed Gas (A) was reacted under the conditions summarized in Table 1 to give the results shown in Table 2.

Comparative Example 3

Using the $Co(Cl)/SiO_2$ catalyst obtained in Example 7, Feed Gas (A) was reacted under the conditions summarized in Table 1 to give the results shown in Table 2.

Comparative Example 4

Granular silica gel (100 g) was placed in a flask and heated at 200° C. for 2 hours under vacuum. After cooling, 6.73 mmol of tetrairidium dodecacarbonyl ($Ir_4(CO)_{12}$) and the mixture was stirred at 150° C. under vacuum. The resulting mixture was then heated at 450° C. under an atmosphere of hydrogen for 3 hours to give an Ir-containing catalyst (named $Ir(CO)/SiO_2$) having an Ir content of 5.16 parts by weight per 100 parts by weight of the silica gel carrier. Using this $Ir(CO)/SiO_2$ catalyst, Feed Gas (A) was reacted under the conditions summarized in Table 1 to give the results shown in Table 2.

Comparative Example 5

Granular silica gel (100 g) was placed in a flask and heated at 200° C. for 2 hours under vacuum. After cooling, an aqueous solution containing 26.9 mmol of iridium chloride and the mixture was stirred at 150° C. under vacuum, dried and treated with hydrogen to give an Ir-containing catalyst (named $Ir(Cl)/SiO_2$) having an Ir content of 5.16 parts by weight per 100 parts by weight of the silica gel carrier. Using this $Ir(Cl)/SiO_2$ catalyst, Feed Gas (A) was reacted under the conditions summarized in Table 1 to give the results shown in Table 2.

TABLE 1

| Experiment No. | Catalyst | Content of Catalytic Components Co | Content of Catalytic Components Ir | Mixed Gas Feed | Pressure ($kg/cm^2$) | Temperature (°C.) |
| --- | --- | --- | --- | --- | --- | --- |
| 1 | Example 1 | 5 | 5.16 | A | 11 | 150 |
| 2 | Example 1 | 5 | 5.16 | A | 11 | 170 |
| 3 | Example 1 | 5 | 5.16 | B | 11 | 150 |
| 4 | Example 1 | 5 | 5.16 | C | 41 | 150 |
| 5 | Example 1 | 5 | 5.16 | C | 31 | 150 |
| 6 | Example 1 | 5 | 5.16 | C | 11 | 150 |
| 7 | Example 2 | 5 | 2.06 | A | 11 | 150 |
| 8 | Example 2 | 5 | 2.06 | A | 11 | 170 |
| 9 | Example 3 | 5 | 5.16 | A | 11 | 170 |
| 10 | Example 4 | 5 | 2.06 | A | 11 | 150 |
| 11 | Example 5 | 5 | 0.50 | A | 11 | 150 |
| 12 | Example 6 | 5 | 2.06 | A | 11 | 150 |
| 13 | Example 6 | 5 | 2.06 | A | 11 | 190 |
| 14 | Example 7 | 5 | 2.06 | A | 11 | 150 |
| 15 | Example 7 | 5 | 2.06 | A | 11 | 170 |
| 16 | Comptv. 1 | 5 | 0 | A | 11 | 170 |
| 17 | Comptv. 2 | 5 | 0 | A | 11 | 170 |
| 18 | Comptv. 3 | 5 | 0 | A | 11 | 170 |
| 19 | Comptv. 4 | 0 | 5.16 | A | 11 | 150 |
| 20 | Comptv. 4 | 0 | 5.16 | A | 11 | 170 |
| 21 | Comptv. 5 | 0 | 5.16 | A | 11 | 150 |
| 22 | Comptv. 5 | 0 | 5.16 | A | 11 | 170 |

TABLE 2

| Experiment No. | Ethylene Conversion (%) | Selectivity (%) Ethane | Propionaldehyde | n-Propanol | Propionic acid | 2-Methyl-2-pentenal | 2-Methylpentanal | 2-Methyl-1-pentanol |
| --- | --- | --- | --- | --- | --- | --- | --- | --- |
| 1 | 32.5 | 57.6 | 29.5 | 7.9 | 0.0 | 1.5 | 2.1 | 1.1 |
| 2 | 55.7 | 61.5 | 15.3 | 18.5 | 0.1 | 0.8 | 1.6 | 1.9 |
| 3 | 8.0 | 48.0 | 45.0 | 3.8 | 0.0 | 2.2 | 0.9 | 0.0 |
| 4 | 10.0 | 29.7 | 32.3 | 5.9 | 0.0 | 16.2 | 6.6 | 0.4 |
| 5 | 5.1 | 32.3 | 53.5 | 1.9 | 0.0 | 8.3 | 3.0 | 0.0 |
| 6 | 3.1 | 36.2 | 59.9 | 2.0 | 0.0 | 1.9 | 0.1 | 0.0 |
| 7 | 28.3 | 51.4 | 34.2 | 6.3 | 0.0 | 5.7 | 2.3 | 0.1 |
| 8 | 61.5 | 61.1 | 19.4 | 15.3 | 0.0 | 1.8 | 2.3 | 0.1 |
| 9 | 46.6 | 75.7 | 9.6 | 13.2 | 0.0 | 0.5 | 0.9 | 0.1 |
| 10 | 10.1 | 67.4 | 24.5 | 1.1 | 0.0 | 5.5 | 1.4 | 0.0 |
| 11 | 12.4 | 52.7 | 35.8 | 5.2 | 0.0 | 5.7 | 0.6 | 0.0 |
| 12 | 1.1 | 67.2 | 23.7 | 2.1 | 0.0 | 6.0 | 1.0 | 0.0 |
| 13 | 11.9 | 66.6 | 20.3 | 8.7 | 0.1 | 3.6 | 0.8 | 0.0 |
| 14 | 1.2 | 78.8 | 16.3 | 2.8 | 0.0 | 1.8 | 0.5 | 0.0 |
| 15 | 2.3 | 78.3 | 16.2 | 2.3 | 0.0 | 2.3 | 0.8 | 0.0 |
| 16 | 0.1 | 97.7 | 1.6 | 0.3 | 0.0 | 0.2 | 0.1 | 0.0 |
| 17 | 3.0 | 82.8 | 12.1 | 1.2 | 0.0 | 3.6 | 0.3 | 0.0 |
| 18 | 0.6 | 81.1 | 15.4 | 3.5 | 0.0 | 0.0 | 0.0 | 0.0 |
| 19 | 0.7 | 87.8 | 9.5 | 2.3 | 0.0 | 0.0 | 0.0 | 0.0 |
| 20 | 0.8 | 87.2 | 10.0 | 2.8 | 0.0 | 0.0 | 0.0 | 0.0 |
| 21 | 1.5 | 79.5 | 11.8 | 8.7 | 0.0 | 0.0 | 0.0 | 0.0 |
| 22 | 2.3 | 80.6 | 8.9 | 10.6 | 0.0 | 0.0 | 0.0 | 0.0 |

EXAMPLE 8

A quantity of the Co(A)/SiO$_2$ catalyst obtained in Example 1 was mixed with an aqueous solution containing 26.9 mmol of ruthenium chloride (RuCl$_3$.xH$_2$O) and the mixture was stirred at 120° C. under vacuum. The resulting mixture was then heated at 450° C. under an atmosphere of hydrogen for 3 hours to give a Co,Ru-containing catalyst (named Co(A)-Ru(Cl)/SiO$_2$) having Co and Ru contents of 5 parts by weight and 2.71 parts by weight, respectively, per 100 parts by weight of the silica gel carrier. The Co was found to present not only as elemental metal but also as ions bonded to oxygen atoms of the silica gel, while the Ru was found to be present as elemental metal.

The Co(A)-Ru(Cl)/SiO$_2$ was packed in a stainless steel tubular reactor. After a further hydrogen treatment at 450° C. for 3 hours, Feed Gas (A) was fed to the reactor at a rate of 30 ml/minute and reacted at 170° C. under 10 atmospheres. The product gas discharged from the reactor was introduced directly into a gas chromatograph to measure the conversion of ethylene and the selectivities. The results are summarized in Table 3.

EXAMPLE 9

A quantity of the Co(A)/SiO$_2$ catalyst obtained in Example 1 was mixed with 8.97 mmol of triruthenium dodecacarbonyl (Ru$_3$(CO)$_{12}$) and the mixture was stirred under vacuum at 120° C. and treated with hydrogen at 450° C. to give a Co,Ru-containing catalyst (named Co(A)-Ru(CO)/SiO$_2$) having a Co content of 5 parts by weight and an Ru content of 2.71 parts by weight per 100 parts by weight of the silica gel carrier. Using this catalyst, Feed Gas (A) was reacted under the same conditions as those in Example 8 to give the results shown in Table 3.

EXAMPLE 10

A quantity of the Co(A)/SiO$_2$ catalyst obtained in Example 1 was mixed with an aqueous solution containining 26.9 mmol of rhodium chloride (RhCl$_3$.xH$_2$O) and the mixture was dried at 120° C. and treated with hydrogen at 450° C. to give a Co,Rh-containing catalyst (named Co(A)-Rh(Cl)/SiO$_2$) having a Co content of 5 parts by weight and a Rh content of 2.76 parts by weight per 100 parts by weight of the silica gel carrier. Using this catalyst, Feed Gas (A) was reacted under the same conditions as those in Example 8 to give the results shown in Table 3.

EXAMPLE 11

A quantity of the Co(A)/SiO$_2$ catalyst obtained in Example 1 was mixed with 6.73 mmol of tetrarhodium dodecacarbonyl (Rh$_4$(CO)$_{12}$). The mixture was stirred under vacuum and treated with hydrogen at 450° C. to give a Co,Rh-containing catalyst (named Co(A)-Rh(CO)/SiO$_2$) having a Co content of 2.76 parts by weight and an Rh content of 5 parts by weight per 100 parts by weight of the silica gel carrier. Using this catalyst, Feed Gas (A) was reacted under the same conditions as those in Example 8 to give the results shown in Table 3.

EXAMPLE 12

A quantity of the Co(A)/SiO$_2$ catalyst obtained in Example 1 was mixed with an aqueous solution containining 26.9 mmol of ammonium perrhenate (NH$_4$ReO$_4$). The mixture was dried at 120° C. and treated with hydrogen at 450° C. to give a Co,Re-containing catalyst (named Co(A)-Re(ON)/SiO$_2$) having a Co content of 5 parts by weight and a Re content of 5 parts by weight per 100 parts by weight of the silica gel carrier. Using this catalyst, Feed Gas (A) was reacted under the same conditions as those in Example 8 to give the results shown in Table 3.

EXAMPLE 13

A quantity of the Co(A)/SiO$_2$ catalyst obtained in Example 1 was mixed with an aqueous solution containining 26.9 mmol of chloroplatinic acid (H$_2$PtCl$_6$.6H$_2$O). The mixture was dried at 120° C. and treated with hydrogen at 450° C. to give a Co,Pt-containing catalyst (named Co(A)-Pt(Cl)/SiO$_2$) having a Co content of 5 parts by weight and a Pt content of 5.24 parts by weight per 100 parts by weight of the silica gel carrier. Using this catalyst, Feed Gas (A) was reacted under the same conditions as those in Example 8 to give the results shown in Table 3.

Example 14

A quantity of the Co(A)/SiO$_2$ catalyst obtained in Example 1 was mixed with an aqueous solution containining 26.9 mmol of diammineplatinum (II) nitrate (Pt(NH$_3$)$_2$(NO$_3$)$_2$) and the mixture was dried at 120° C. and treated with hydrogen at 450° C. to give a Co,Pt-containing catalyst (named Co(A)-Pt(N)/SiO$_2$) having a Co content of 5 parts by weight and a Pt content of 5.24 parts by weight per 100 parts by weight of the silica gel carrier. Using this catalyst, Feed Gas (A) was reacted under the same conditions as those in Example 8 to give the results shown in Table 3.

EXAMPLE 15

A quantity of the Co(A)/SiO$_2$ catalyst obtained in Example 1 was mixed with an aqueous solution containining 0.14 mmol of diamminepalladium (II) nitrate (Pd(NH$_3$)$_2$(NO$_3$)$_2$). The mixture was dried at 120° C. and treated with hydrogen at 450° C. to give a Co,Pd-containing catalyst (named Co(A)-Pd(NN)/SiO$_2$) having a Co content of 5 parts by weight and a Pd content of 0.027 parts by weight per 100 parts by weight of the silica gel carrier. Using this catalyst, Feed Gas (A) was reacted under the same conditions as those in Example 8 to give the results shown in Table 3.

EXAMPLE 16

A quantity of the Co(A)/SiO$_2$ catalyst obtained in Example 1 was mixed witch an aqueous solution containining 12.9 mmol of copper acetate monohydrate (Cu(OCOCH$_3$)$_2$.H$_2$O). The mixture was dried at 120° C. and treated with hydrogen at 450° C. to give a Co,Cu-containing catalyst (named Co(A)-Cu(A)/SiO$_2$) having a Co content of 5 parts by weight and a Cu content of 0.82 parts by weight per 100 parts by weight of the silica gel carrier. Using this catalyst, Feed Gas (A) was reacted under the same conditions as those in Example 8 to give the results shown in Table 3.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

TABLE 3

| Example No. | Ethylene Conversion (%) | Selectivity (%) | | | | | | |
|---|---|---|---|---|---|---|---|---|
| | | Ethane | Propion- aldehyde | n-Propanol | Propionic acid | 2-Methyl- 2-pentanal | 2-Methyl- pentanal | 2-Methyl- 1-pentanol |
| 8 | 21.2 | 66.2 | 14.8 | 16.1 | 0.7 | 1.5 | 0.3 | 0.4 |
| 9 | 19.8 | 70.2 | 17.3 | 4.8 | 0.0 | 6.7 | 0.9 | 0.0 |
| 10 | 42.8 | 41.1 | 47.4 | 3.7 | 0.9 | 5.9 | 0.3 | 0.7 |
| 11 | 47.2 | 33.9 | 44.6 | 9.3 | 0.8 | 9.4 | 0.8 | 1.0 |
| 12 | 25.6 | 56.8 | 22.8 | 9.6 | 1.0 | 8.1 | 1.0 | 0.6 |
| 13 | 27.9 | 56.3 | 7.9 | 34.5 | 0.0 | 0.5 | 0.4 | 0.5 |
| 14 | 25.3 | 42.3 | 19.7 | 31.2 | 0.3 | 3.6 | 1.6 | 1.3 |
| 15 | 32.2 | 25.8 | 12.9 | 12.0 | 0.0 | 41.2 | 0.4 | 0.5 |
| 16 | 8.5 | 65.3 | 10.8 | 1.4 | 4.5 | 15.6 | 2.1 | 0.0 |

What is claimed is:

1. A catalyst for the hydroformylation reaction of olefin, carbon monoxide and hydrogen to form alcohols and aldehydes, said catalyst consisting essentially of a silica gel carrier, and 0.1–10% by weight of two or more catalytic metal components, based on the weight of said carrier, supported on said carrier, the metals of said catalytic metal components being a combination of, in their elemental states, cobalt and at least one auxiliary metal selected from the group consisting of rhodium, ruthenium, iridium, copper, osmium and gold.

2. A catalyst as claimed in claim 1, wherein said cobalt and said auxiliary metal are present in such a proportion as to provide an auxiliary metal to cobalt atomic ratio of 0.001–10.

* * * * *